(12) United States Patent
Swensgard et al.

(10) Patent No.: US 8,245,899 B2
(45) Date of Patent: Aug. 21, 2012

(54) DRIVEN SURGICAL STAPLER IMPROVEMENTS

(75) Inventors: Brett E. Swensgard, West Chester, OH (US); Ryan J. Laurent, Liberty Township, OH (US); Bret W. Smith, Kings Mills, OH (US); David C. Yates, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 233 days.

(21) Appl. No.: 12/693,462

(22) Filed: Jan. 26, 2010

(65) Prior Publication Data
US 2011/0024479 A1 Feb. 3, 2011

Related U.S. Application Data

(60) Provisional application No. 61/150,391, filed on Feb. 6, 2009.

(51) Int. Cl.
*A61B 17/068* (2006.01)
(52) U.S. Cl. .................... 227/176.1; 227/19
(58) Field of Classification Search ............... 227/176.1, 227/19, 175.1
See application file for complete search history.

(56) References Cited

U.S. PATENT DOCUMENTS

| | | | |
|---|---|---|---|
| 5,383,880 A | 1/1995 | Hooven | |
| 5,403,312 A | 4/1995 | Yates et al. | |
| 5,433,721 A | 7/1995 | Hooven et al. | |
| 5,465,895 A | 11/1995 | Knodel et al. | |
| 5,518,163 A | 5/1996 | Hooven | |
| 5,518,164 A | 5/1996 | Hooven | |
| 5,667,517 A | 9/1997 | Hooven | |
| 5,688,270 A | 11/1997 | Yates et al. | |
| 5,709,680 A | 1/1998 | Yates et al. | |
| 5,782,397 A * | 7/1998 | Koukline | 227/176.1 |
| 5,792,165 A * | 8/1998 | Klieman et al. | 606/170 |
| 5,954,259 A * | 9/1999 | Viola et al. | 227/176.1 |
| 6,646,307 B1 | 11/2003 | Yu et al. | |
| 6,716,223 B2 | 4/2004 | Leopold et al. | |

(Continued)

FOREIGN PATENT DOCUMENTS
EP 0634144 A1 1/1995
(Continued)

OTHER PUBLICATIONS

International Search Report dated May 17, 2010; International Application No. PCT/US2010/022365.

(Continued)

*Primary Examiner* — Brian D Nash
(74) *Attorney, Agent, or Firm* — Dean L. Garner

(57) ABSTRACT

A surgical fastener apparatus including a handle, an elongated shaft having a proximal end attached to the handle and a distal end extending therefrom. An end effector comprising a pair of jaws pivoted at a proximal end thereof and movable between an open and closed position, and a cartridge containing a plurality of surgical fasteners, the cartridge attached to the end effector. An electrically powered actuator for deploying the surgical fasteners. An electrically activated reverse mechanism for moving the elongated member from a distal most position within the end effector to a proximal position, the electrically activated reverse mechanism moves the elongated member proximally after the elongated member has moved to the distal most position by moving the trigger to the open position, and wherein after activation of the reverse mechanism proximal movement of the elongated member can be stopped by returning the trigger to its closed position.

1 Claim, 1 Drawing Sheet

U.S. PATENT DOCUMENTS

| | | |
|---|---|---|
| 7,000,818 B2 | 2/2006 | Shelton, IV et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,568,603 B2 | 8/2009 | Shelton, IV et al. |
| 2004/0094597 A1* | 5/2004 | Whitman et al. .......... 227/180.1 |
| 2004/0232196 A1 | 11/2004 | Shelton, IV et al. |
| 2005/0131390 A1* | 6/2005 | Heinrich et al. ................ 606/1 |
| 2005/0173490 A1 | 8/2005 | Shelton, IV |
| 2006/0025809 A1 | 2/2006 | Shelton, IV |
| 2006/0151567 A1* | 7/2006 | Roy .......................... 227/175.1 |
| 2006/0278680 A1* | 12/2006 | Viola et al. ................. 227/176.1 |
| 2007/0102452 A1 | 5/2007 | Shelton, IV et al. |
| 2007/0102453 A1 | 5/2007 | Morgan et al. |
| 2007/0125956 A1 | 6/2007 | Buschbeck et al. |
| 2007/0158385 A1 | 7/2007 | Hueil et al. |
| 2007/0175949 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1* | 8/2007 | Swayze et al. ............. 227/178.1 |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0233053 A1* | 10/2007 | Shelton et al. .................... 606/1 |
| 2008/0029577 A1* | 2/2008 | Shelton et al. ............. 227/176.1 |
| 2008/0114385 A1 | 5/2008 | Byrum et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167736 A1 | 7/2008 | Swayze et al. |
| 2008/0296346 A1 | 12/2008 | Shelton, IV et al. |
| 2008/0300580 A1 | 12/2008 | Shelton, IV et al. |
| 2009/0206124 A1 | 8/2009 | Hall et al. |
| 2009/0206132 A1 | 8/2009 | Hueil et al. |
| 2009/0206134 A1 | 8/2009 | Swayze et al. |
| 2010/0049084 A1 | 2/2010 | Nock et al. |
| 2010/0089974 A1 | 4/2010 | Shelton, IV |

FOREIGN PATENT DOCUMENTS

| | | |
|---|---|---|
| EP | 0552050 B1 | 5/2000 |
| EP | 1813202 A1 | 8/2007 |
| EP | 1943955 A2 | 7/2008 |
| EP | 1970014 A1 | 9/2008 |
| EP | 2090243 B1 | 6/2011 |

OTHER PUBLICATIONS

International Search Report dated Oct. 12, 2011; International Application No. PCT/US2011/045319.

* cited by examiner

DRIVEN SURGICAL STAPLER IMPROVEMENTS

REFERENCE TO RELATED APPLICATIONS

This application claims the benefit of U.S. Provisional Application Ser. No. 61/150,391 entitled "Motor-Driven Surgical Stapler Improvements" to Ryan J. Laurent, filed on 6 Feb. 2009.

BACKGROUND

An example of a surgical stapler suitable for endoscopic applications is described in U.S. Pat. No. 5,465,895 (which is hereby incorporated herein by reference), which discloses an endocutter with distinct closing and firing actions. An example of a motor driven surgical stapler is U.S. Publication No. 2007/0175958 (which is hereby incorporated herein by reference) in-which excerpts are presented here to detail its base functions, improvements, background, and components. At the end additional improvements to the system are disclosed.

Quote from background and summary of invention from US2007015958—"A clinician using this device is able to close the jaw members upon tissue to position the tissue prior to firing. Once the clinician has determined that the jaw members are properly gripping tissue, the clinician can then fire the surgical stapler with a single firing stroke, or multiple firing strokes, depending on the device. Firing the surgical stapler causes severing and stapling the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. One known solution to lower FTF it use C02 or electrical motors. These devices have not faired much better than traditional hand-powered devices, but for a different reason. Surgeons typically prefer to experience proportionate force distribution to that being experienced by the end-effector in the forming the staple to assure them that the cutting/stapling cycle is complete, with the upper limit within the capabilities of most surgeons (usually around 15-30 lbs). They also typically want to maintain control of deploying the staple and being able to stop at anytime if the forces felt in the handle of the device feel too great or for some other clinical reason. These user-feedback effects are not suitably realizable in present motor-driven endocutters. As a result, there is a general lack of acceptance by physicians of motor-drive endocutters where the cutting/stapling operation is actuated by merely pressing a button.

SUMMARY

In one general aspect, the present invention is directed to a motorized surgical cutting and fastening instrument that provides feedback to the user regarding the position, force and/or deployment of the end effector. The instrument, in various embodiments, also allows the operator to control the end effector, including being able to stop deployment if so desired. The instrument may include two triggers in its handle—a closure trigger and a firing trigger—with separate actuation motions. When an operator of the instrument retracts the closure trigger, tissue positioned in the end effector may be clamped by the end effector. Then, when the operator retracts the firing trigger, a motor may power, via a gear drive train, a rotational main drive shaft assembly, which causes a cutting instrument in the end effector to severe the clamped tissue.

In various embodiments, the instrument may comprise a power assist system with loading force feedback and control to reduce the firing force required to be exerted by the operator in order to complete the cutting operation. In such embodiments, the firing trigger may be geared into the gear drive train of the main drive shaft assembly. In that way, the operator may experience feedback regarding the force being applied to the cutting instrument. That is, the loading force on the firing trigger may be related to the loading force experienced by the cutting instrument. Also in such embodiments, because the firing trigger is geared into the gear drive train, force applied by the operator may be added to the force applied to the motor.

According to various embodiments, when the firing trigger is retracted an appropriate amount (e.g., five degrees), an on/off switch may be actuated, which sends a signal to the motor to rotate at a specified rate, thus commencing actuation of the drive shaft assembly and end effector. According to other embodiments, a proportional sensor may be used. The proportional sensor may send a signal to the motor to rotate at a rate proportional to the force applied to the firing trigger by the operator. In that way, the rotational position of the firing trigger is generally proportional to where the cutting instrument is in the end effector (e.g., fully deployed or fully retracted). Further, the operator could stop retracting the firing trigger at some point in the stroke to stop the motor, and thereby stop the cutting motion. In addition, sensors may be used to detect the beginning of the stroke of the end effector (e.g., fully retracted position) and the end of the stroke (e.g., fully deployed position), respectively. Consequently, the sensors may provide an adaptive control system for controlling end effector deployment that is outside of the closed loop system of the motor, gear drive train, and end effector.

In other embodiments, the firing trigger may not be directly geared into the gear drive train used to actuate the end effector. In such embodiments, a second motor may be used to apply forces to the firing trigger to simulate the deployment of the cutting instrument in the end effector. The second motor may be controlled based on incremental rotations of the main drive shaft assembly, which may be measured by a rotary encoder. In such embodiment, the position of the rotational position of the firing trigger may be related to the position of the cutting instrument in the end effector. Additionally, an on/off switch or a proportional switch may be used to control the main motor (i.e., the motor that powers the main drive shaft).

In various implementations, the end effector may use a helical drive screw in the base of the end effector to drive the cutting instrument (e.g., knife). Also, the end effector may include a staple cartridge for stapling the severed tissue. According to other embodiments, other means for fastening (or sealing) the severed tissue may be used, including RF energy and adhesives.

Also, the instrument may include a mechanical closure system. The mechanical closure system may include an elongate channel having a clamping member, such as an anvil, pivotably connected to the channel to clamp tissue positioned in the end effector. The user may activate the clamping action of the end effector by retracting the closer trigger, which, through a mechanical closure system, causes the clamping action of the end effector. Once the clamping member is locked in place, the operator may activate the cutting operation by retracting the separate firing trigger. This may cause the cutting instrument to travel longitudinally along the channel in order to cut tissue clamped by the end effector.

In various implementations, the instrument may include a rotational main drive shaft assembly for actuating the end effector. Further, the main drive shaft may comprise an articulating joint such that the end effector may be articulated. The articulation joint may comprise, for example, a bevel gear assembly, a universal joint, or a flexible torsion cable capable of transmitting torsion force to the end effector.

Other aspects of the present invention are directed to various mechanisms for locking the closure trigger to a lower, pistol-grip portion of the handle. Such embodiments free up space in the handle directly above and behind the triggers for other components of the instrument, including components of the gear drive train and the mechanical closure system."

The disclosure herein shows how one could embody a battery powered gear driven self-contained endoscopic stapling device.

DETAILED DESCRIPTION OF THE INVENTION

Figure 1:
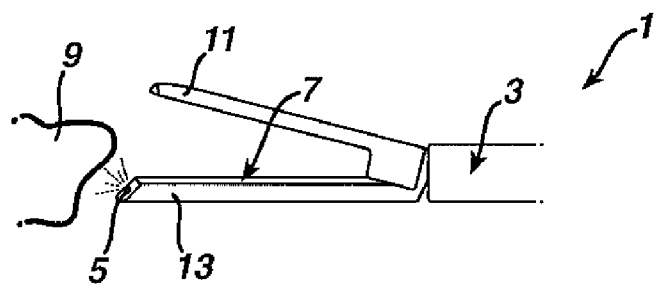
FIG. 1 is a perspective view of a distal end of surgical stapler in accordance with the present invention.
Figure 2:
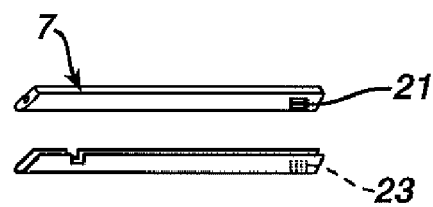
FIG. 2 is a perspective view of a distal end of surgical stapler in accordance with the present invention with the cartridge removed from the channel.
Figure 3:
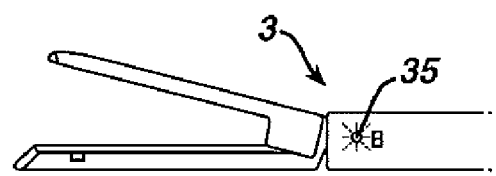
FIG. 3 is a view of a distal end of surgical stapler in accordance with the present invention similar to FIG. 1 showing a lockout indicator.
Figure 4:
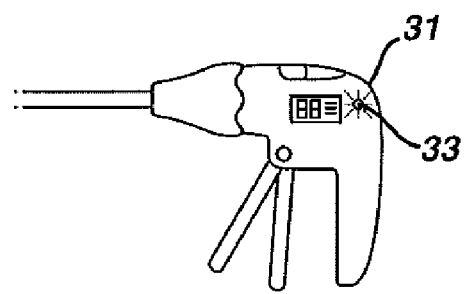
FIG. 4 is a perspective view of a proximal end of surgical stapler in accordance with the present invention.

End-effector illumination Methods/Surgical site illumination with a powered endocutter: Currently when the end-effector is in or near its deployment position it is sometimes difficult for the surgeon to visualize the treatment site as there are shadows cast by adjacent structures as well as the end-effector may even be behind another structure entirely. Shown in FIG. 1, is a distal end 3 of a surgical stapler 1 in accordance with the present invention, including anvil 11, cartridge body 7, and channel 13. As seen from that figure, an additional light source 5 could be positioned on the end of the cartridge body 7 to illuminate tissue 9. This light source could be any combination of practical means that convert electrical energy to light including but not limited to semiconductor (such as LED), a conventional incandescent or filament bulb, electroluminescent or laser. This would allow the surgeon to not only light up the treatment site directly, it could allow for backlighting of structures to see the internal components like vasculature or with a laser pointer allow the surgeon to point out areas of interest to other via the traditional scope.

This would be very easy to do by allowing one or more contacts 21 on the back of the cartridge 7 that would engage contacts 23 within the channel. This would allow the surgeon to energize the light as needed by energizing contact set via a switch positioned on the handle 31. This switch could even have variable intensity as the one described in could control the actuation speed of the main, device.

As noted above, U.S. publication 2007/0175949 further discloses in FIGS. 45-47 output displays that could show among other this position feedback of the end-effector, lockout status, number of firings etc. This would minimize one of the more difficult issues for the user, which is the identification of the status of a device, especially the lockout status of the device without actuating the device. An additional feedback that would be helpful for the user would be immediate feedback as to the status of the cartridge when it is loaded. As in the above application it could be rolled up into the lockout indication on the handle 31. An indicator 33 (such as an LED, glass bulb, LCD, sonic enunciator, vibrator, etc.) could solely be associated with the status of a cartridge lockout means or mechanism such that it providing this information to the surgeon. This LED could be located on the handle. Alternatively an indicator 35 could be located near the distal end 3 which would provide immediate information to the surgeon and loader if the cartridge is "good to go" or not. This can be accomplished with a switch or set of contacts associated directly with the mechanical lockout. The switch or contacts complete a circuit such that the indicator provides appropriate information. This completed contact set could be through a conductive element within the sled (part 33 in the publication 20070175958) and the two contacts could be in the proximal position of the channel (part 22). Another way to detect lockout status is indirectly through instrument status (example I: loaded cartridge and no attempt to fire would indicate lockout is not engaged; example 2: fired instrument and no new cartridge installed would indicate lockout is engaged; etc.) Another embodiment would be to place the LED or visual indication cue on the cartridge itself. When the cartridge is snapped into place it creates a contact that supplies the cartridge with power. Should the cartridge be fired not only does the mechanical lockout stop the advancement of the knife the cartridge circuit light up the LED on the cartridge informing the surgeon on the scope monitor that the cartridge is locked out. This could be further expanded by placing a small battery or other charge accumulator within the cartridge itself to eliminate the need for a power connection to the main device. Also the cartridge circuit could be set to light the lockout light whenever the device is closed to inform the user there is a spent cartridge in the device.

Indication feedback for powered articulation and cartridge color: Indicating the type of cartridge installed (color) and angle of articulation is considered useful to the surgeon. The indication of articulation angle could be indicated in several ways including numerically or graphically as in an arc of LEDs. The location of this indication could be on the handle in a convenient location or on the shaft of the device just proximal to the end-effector. The end-effector feedback could be passive or active. The active would light up additional LEDs to show the angle. The passive could just show a half pie lighted up so the surgeon could intuit how articulated the end-effector is. As we further explore the surgical procedures it becomes more and more obvious that the surgeon's eyes need to be on the surgical site not on the handle of the instrument. We also begin to understand the surgeon's need for complete status feedback from the device. Articulation angle could be illuminated as part of the articulation joint itself. With lights, LEDs, etc. denoting the differing angle or even a small LCD denoting angle in degrees. This would allow the surgeon to have some feedback on the angle off of straight so he/she can easily navigate back to this angle after removal and reinsertion. Another issue is "obvious" indication of what color cartridge is in the device. 'This can be accomplished by a color coded light array on either the end-effector or the cartridge. This information could also be transmitted back to the handle to display a "redundant" display to assure there is minimal confusion as to what cartridge is in the jaws. Another improvement could include a small leaf spring contact connected to the proximal deck of the cartridge that indicates if a minimum tissue pressure has been achieved within the jaws. This minimum pressure would at the very least indicate if a thick tissue cartridge is being used in thin tissue applications, as it would not light if insufficient tissue pressure on the deck were present.

Automatic advancement and retraction of an electrical endocutter: There are several steps within the function of a stapler that must be accomplished in an established order. Once the closure trigger is clamped actuation of the firing cycle is the next necessary step. After for actuation then retraction of the system is the next sequential step. With the inclusion of a power source other than the user (i.e. batteries or pneumatics) the ability to reduce user initiated steps (and therefore device complexity) the system itself can begin to accomplish these steps itself. Internal switches or circuits could be added to allow for these steps to automatically be initiated. The next challenge is to allow for the user to intuitively be able to delay, slow or stop the automatic actuations. For instance, the same actuation button that would allow for firing initiation in a tactile feedback device like Ser. No. 11/344,035 could be used to slow or stop an automatic return system by the user depressing the button during the retraction. Once pressure was removed from the button the auto-return would recommence. The same could be for auto-firing where if the system did not require a button to, fire, but a control was provided that moved with the knife motion that the user could depress that would stop or slow its deployment but would be unnecessary if the system was see to be running correctly.

Accidental actuation prevention I Accidental actuation prevention for a powered endocutter: With the introduction of powered systems that no longer limit the device function to the force capabilities of the user, inadvertent initiation of the firing cycle may become a much more prevalent issue. It will be increasing ease to "bump" the activation control and have the instrument begin firing thereby tripping the lockout of the cartridge or even "jamming" it on tissue, as the user is unaware it has already begun firing. To eliminate this issue secondary unlock activator switches or buttons could be used to unlock the firing mechanism. This is much the same as the two switch systems used in the power saw industry as well as the military to protect against accidental actuation. The secondary switch can either release the lock on the firing trigger or merely energize the power to the control.

Use of a non-sterile battery within a sterilized device I Packaging as a sterility barrier for battery pack reuse: There is a. possible need of a method for the introduction of non-sterile battery packs (possibly with the electronics integral to the battery pack if programmable logic becomes a key customer need). A patent already exists within the orthopedic drill industry for the insertion of a non-sterile battery pack within a separately sterilized re-useable device. This innovation is intended to improve that concept by utilizing the disposable device sterile packaging to protect the sterility of the instrument during the insertion of the non-sterile battery pack. A further improvement would be the inclusion of a "hatch" door designed within the instrument and closable after the pack has been inserted but before the device is removed from the final sterile packaging. This hatch would then "contain" the non-sterile battery that could contaminate the sterile surgical field. The method here would be to include an additional layer of packaging that would have a perforated area that the battery could be pushed through, either rupturing the extra layer and allowing the battery through or going with the electrode set of the battery only to be ruptured by the exposable pin tips of the battery at complete insertion. An alternative of this would be to have the internal terminals of the gun (deep inside the battery protection cavity) rupture the sterile barrier and seat within pinholes in the battery pack. The hatch could then be closed through the sterile pack sealing the system. The gun could then be handed into the sterile field normally as any sterile device could.

Position Locator Embodiments I Linear encoder and load control of motor parameters: U.S. Pat. Nos. 6,646,307 and 6,716,223 disclose the mechanisms for the measurement of rotation and related torque to control motor parameters and optimizing of those parameters based on identification of end-effector configurations and loading. US publication 20070175958 shows a method through the use of a threaded length of the primary shaft in FIGS. 8-13 how this type of linear motion control could be used to control the trigger location. The same type of method could be used for electronic linear control methods. The end-effector could identify its length and type mechanically by depressing at least one spring biased plunger, which could identify to the handle the type, and length it would allow the motor to run. The motor rotation could be converted from rotatory motion to linear rack or cable motion, which could then be used to adjust motor voltage, current, and speed to affect the desired linear motion of the control slide. The control slide could then be directly coupled to the knife drive motion. This control slide could have discrete or continuous "stop" locations that the plunger identifier marks as the max "go to" linear displacement before retraction.

Identification of modular reloads with linear drive: A useful feature for a surgical instrument is the ability to identify which end-effector has been attached to the instrument. In the case of a powered surgical stapler, several different types of end-effectors could be attached. Additionally, a type of end-effector may have at least one function and/or feature that is selectively utilized or enabled. Disclosed are means for identifying which end-effector is attached. Note that the "type" of Endeffector referenced below is not limited to mechanical, pneumatic or hydraulically coupled end-effectors. The instrument may take different actions, adjust operating parameters, indicate available functions etc. as a result of detecting this end effector.

The end-effector has an electrical connection that is made when it is attached to the instrument. The instrument communicates with the end-effector and reads at least one of several types of signals. A switch position or contact position indicates which type of end-effector is present. A passive element is measured for impedance and the result indicates which type of end-effector is present.

The end-effector has a radio frequency link to the instrument and data is transferred in at least one direction between the end-effector and the instrument.

The end-effector has an acoustic link to the instrument and data is transferred in at least one direction between the end-effector and the instrument.

The end-effector has an optical link to the instrument and data is transferred in at least one direction between the end-effector and the instrument.

The end-effector has mechanical link that engages elements (such as switches or contacts) in the instrument that identify it and thereby data is transferred in at least one direction between the end-effector and the instrument.

Active adjustable staple height for a powered endocutter: Staple height that is adjustable to the tissue thickness and type has been pursued for many years. Most recently Ser. Nos. 11/231,456 and 11/540,735 are around a flexible coupling member or supports that would allow the gap of the instrument to enlarge with loads induced by thicker tissue in the device. This "passive" variable staple height allows the thickness of the tissue to create larger staple forms. With the introduction of a power source within the instrument this allows for the use of electricity to change the height of an internal element within the dynamic coupling element with would change the height of the staple "actively" by the surgeon or instrument setting the desired height. This internal element could be a shape memory material and the electricity changes its temperature and therefore allows it to change its physical height due to preset configuration. Another viable method would be the inclusion of an electro-active polymer (EAP) that through the introduction of an electric field allows it to change its height and width. Yet a third embodiment would be to utilize a traditional linear electrical stepper element that can ratchet a small adjustable screw element within the coupling beam that would adjust its height.

What is claimed:

1. A surgical fastener apparatus comprising:
   a. a handle, an elongated shaft having a proximal end attached to said handle and a distal end extending therefrom, an end effector comprising a pair of jaws pivoted at a proximal end thereof and movable between an open and closed position, and a cartridge containing a plurality of surgical fasteners, said cartridge attached to said end effector;
   b. an electrically powered actuator for deploying said surgical fasteners, said actuator comprising a power source and a motor, said actuator including an elongated member extending through said shaft and movable distally into said end effector for deploying said staples and proximally back out of said end effector;
   c. a trigger attached to said handle and having an open and closed position; and said trigger for activating said actuator when in said closed position; and
   d. an electrically activated reverse mechanism for moving said elongated member from a distal most position within said end effector to a proximal position, said electrically activated reverse mechanism moves said elongated member proximally, after said elongated member has moved to said distal most position, by moving said trigger back to said open position, and wherein after activation of said reverse mechanism and while said reverse mechanism is moving said trigger back to said open position, proximal movement of said elongated member can be stopped by returning said trigger to its closed position.

* * * * *